(12) United States Patent
Li et al.

(10) Patent No.: US 9,233,116 B2
(45) Date of Patent: Jan. 12, 2016

(54) COMPOSITION CONTAINING IRIDOIDS AND USES THEREOF

(75) Inventors: Lin Li, Beijing (CN); Linlin Yin, Beijing (CN); Lan Zhang, Beijing (CN); Wen Wang, Beijing (CN); Ruyi Zhang, Beijing (CN)

(73) Assignee: XUANWU HOSPITAL OF CAPITAL MEDICAL UNIVERSITY, Beijing (CN)

( * ) Notice: Subject to any disclaimer, the term of this patent is extended or adjusted under 35 U.S.C. 154(b) by 194 days.

(21) Appl. No.: 13/703,170

(22) PCT Filed: Dec. 15, 2010

(86) PCT No.: PCT/CN2010/002049
§ 371 (c)(1),
(2), (4) Date: Jan. 22, 2013

(87) PCT Pub. No.: WO2011/153678
PCT Pub. Date: Dec. 15, 2011

(65) Prior Publication Data
US 2013/0116205 A1 May 9, 2013

(30) Foreign Application Priority Data
Jun. 11, 2010 (CN) .......................... 2010 1 0198166

(51) Int. Cl.
*A01N 43/04* (2006.01)
*A61K 31/70* (2006.01)
*C07H 15/24* (2006.01)
*A61K 31/7048* (2006.01)
*A61K 36/40* (2006.01)

(52) U.S. Cl.
CPC ............. *A61K 31/7048* (2013.01); *A61K 36/40* (2013.01)

(58) Field of Classification Search
CPC ........................... A61K 36/40; A61K 31/7048
See application file for complete search history.

(56) References Cited

FOREIGN PATENT DOCUMENTS

| CN | 1566124 | 1/2005 |
|---|---|---|
| CN | 101254185 | 9/2008 |
| CN | 101843630 | 9/2010 |

OTHER PUBLICATIONS

Li et al., "The Pharmacological Effects of Morroniside and Loganin Isolated from Linweidihuang Wan, on MC3T3-E1 Cells," Molecules, 15, 7403-7414 (2010).*
(S) McCarthy et al, "Mouse Models of Multiple Sclerosis: Experimental Autoimmune Encephalomyelitis and Theiler's Virus-Induced Demyelinating Disease," Methods in Molecular Biology, 900, 381-401 (2012).*
Extended Supplementary Search Report for corresponding EP Application No. 10 852 671.6 mailed Nov. 11, 2013.

* cited by examiner

*Primary Examiner* — Lawrence E Crane
(74) *Attorney, Agent, or Firm* — Kilpatrick Townsend & Stockton LLP

(57) ABSTRACT

Composition containing iridoids such as morroniside and loganin, the use thereof in preparing medicaments for preventing and treating neurologic demyelinating diseases, and the method thereof in treating diseases related to neurologic demyelinating lesions are disclosed by the present application.

19 Claims, No Drawings

COMPOSITION CONTAINING IRIDOIDS AND USES THEREOF

CROSS-REFERENCE TO RELATED APPLICATIONS

This application is a US national stage application of PCT/CN2010/002049 filed Dec. 15, 2010, which claims priority to Chinese Patent Application No. 201010198166.0, filed Jun. 11, 2010, the entireties of which are incorporated herein by reference.

TECHNICAL FIELD

The present invention relates to a novel use of a composition comprising an iridoid compound for prophylaxis or treatment of a nervous system disease and, a pharmaceutical composition comprising said composition, and a method of using the compound or the pharmaceutical composition for prophylaxis or treatment of a nervous system disease.

BACKGROUND ART

Myelin sheath is a layer of lipid cell membrane that covers sheath nerve fiber axon outside and consists of myelin sheath cells, which main physiological function is to act "insulation" and protection functions on nerve axon, and facilitates rapid transmission of nervous impulse. Demyelinating disease is a group of disorders featured with myelinoclasis of nerve fiber as main pathological change, which can either implicate central nervous system, or peripheral nervous system. This disease has main pathological features of: (1) nerve fiber myelinoclasis, presented in multiple small disseminated foci, or a relatively large focus formed by one or more foci in fusion; (2) demyelination lesions are distributed in alba, spinal cord or peripheral nerves, infiltrating in coatsleeve like form along inflammatory cells around veinlet.

This kind of diseases include multiple sclerosis, optical neuromyelitis, acute disseminated encephalomyelitis, diffuse sclerosis, concentric circle sclerosis, leukodystrophy, central pontine myelinolysis, acute inflammatory demyelinating polyneuropathy, chronic inflammatory demyelinating polyneuropathy; and demyelinating diseases caused by other factors, including but not limited to leukoencephalopathy caused by ischemia-anoxia diseases, subacute combined degeneration caused by nutrition deficiency diseases, subacute sclerosing panencephalitis or progressive multifocal leukoencephalopathy caused by viral infection, diabetic neuropathy (this disease is mainly presented demyelination lesion), nervous lesions of systemic lupus erythematosus (this disease is mainly presented in demyelination lesion). The research of an effective drug for alleviating myelination and promoting myelin sheath plerosis may provide an important means for preventing demyelination diseases in central and peripheral nervous systems caused by various factors.

Iridoids are a group of specific monoterpene compounds, which mother nuclei are all in ring form, having ethylenic linkage and ether linkage, and which basic skeletons are of the following structure formula.

1. Basic skeletons of iridoids

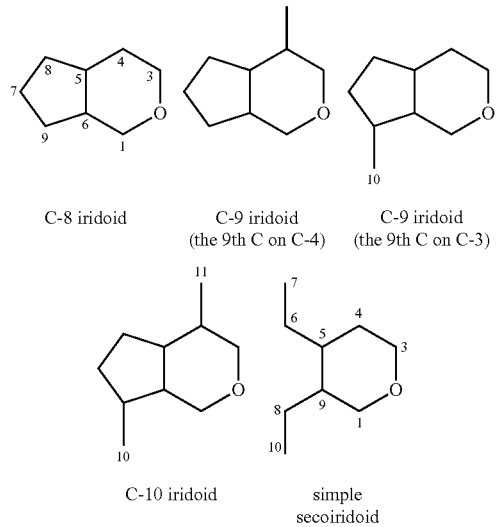

C-8 iridoid   C-9 iridoid (the 9th C on C-4)   C-9 iridoid (the 9th C on C-3)

C-10 iridoid   simple secoiridoid

In the molecules of iridoids, $C_1$—OH is very active, easy to bind to a saccharide, and most of natural iridoids are glycosides, especially D-glucosides. They include but are not limited to:

(1) Common iridoid glycosides: 1) C-8 iridoid glycosides; 2) C-9 iridoid glycosides (the $9^{th}$ C links to C-4); 3) C-9 iridoid glycosides (the $9^{th}$ C links to C-8); 4) C-10 iridoid glycosides. The examples are morroniside, loganin, 6'-acetylasperuloside, geniposide, catalpol, allamdin, allamandin, asperuloside, aucubin, catalpin, deoxyloganin, genipin, plumericin, verbenalin, kingiside.

(2) Diffractive ring iridoid glycosides: such as gentiopicrin, amarogentin, secologanin, swertiamarin.

(3) Valeriana type iridoids, such as 7,10,2'-3 acetylpatrinoside, and 10-acetylpatrinoside.

(4) Plumeria type iridoids: such as poncirin A.

(5) Iridoids with oxo bridge between 3- and 10-positions, such as iridoid glycosides with oxo bridge between 3- and 10-positions, crescent glycoside B.

(6) Iridoids related to nepetalactone type, such as ipuranol.

(7) Transformative iridoids, such as crescent glycosides A and B, poncirin B with ternary oxaspiro structure at 8-position.

(8) Formed with several iridoids directly via ester bond or via linkage of terpenes, phenols. Examples are acevaltratum, deacetylasperuloside acid methyl ester.

The inventors of the present invention conduct wide and deep researches on iridoid compounds such as morroniside and loganin, and find the iridoid compounds have function of alleviating myelinoclasis and inflammatory cell infiltration in nervous system, and promoting myelination and plerosis, and thus the present invention is carried out.

CONTENTS OF THE INVENTION

One aspect of the present invention provides a use of an iridoid compound such as morroniside and/or loganin in the manufacture of a medicament for treatment of a demyelinating disease of nervous system. Another aspect of the present invention also provides a pharmaceutical composition comprising an iridoid compound, and a method of using the compound or the pharmaceutical composition for treatment of a demyelinating disease of nervous system.

More specifically, according to one embodiment of the present invention, the present invention provides:

1. A use of a composition comprising an iridoid compound in the manufacture of a medicament for alleviating or repairing a disease associated with nervous system myelin sheath lesion.

2. According to another embodiment of the present invention, wherein the iridoid compound is morroniside or its homolog or analog, and/or loganin or its homolog or analog.

3. According to another embodiment of the present invention, wherein morroniside is 25-50% w/w of the composition, and loganin is 25-40% w/w of the composition.

4. According to another embodiment of the present invention, wherein the composition is an extract of Fructus corni, wherein morroniside is 25-50 wt % relative to the total weight of the extract, and loganin is 25-40 wt % relative to the total weight of the extract.

5. According to another embodiment of the present invention, wherein the alleviating nervous system myelin sheath lesion is used for the treatment of a disease with myelin sheath lesion caused by various reasons, or for the treatment of a demyelinating disease of nervous system.

6. According to another embodiment of the present invention, wherein the disease is multiple sclerosis, optical neuromyelitis, acute disseminated encephalomyelitis, diffuse sclerosis, concentric circle sclerosis, leukodystrophy, central pontine myelinolysis, acute inflammatory demyelinating polyneuropathy or chronic inflammatory demyelinating polyneuropathy, or the disease is leukoencephalopathy caused by an ischemia-anoxia disease, subacute combined degeneration caused by a nutrition deficiency disease, subacute sclerosing panencephalitis or progressive multifocal leukoencephalopathy caused by a viral infection.

7. According to another embodiment of the present invention, wherein the disease is diabetic neuropathy or systemic lupus erythematosus.

According to another embodiment of the present invention, the present invention also provides:

8. A pharmaceutical composition for treatment or prophylaxis of a demyelinating disease of nervous system, characterized in that it comprises the composition according to any one of embodiments 1-4 and optionally a pharmaceutically acceptable carrier.

According to another embodiment of the present invention, the present invention also provides:

9. A method for treatment or prophylaxis of a demyelinating disease of nervous system, comprising administering a patient in need thereof a therapeutically effective amount of the composition according to any one of embodiments 1-4, or a pharmaceutical composition comprising the composition.

10. The pharmaceutical composition according to the embodiment 8 or the method according to embodiment 9, wherein the disease is any one of diseases of any one of embodiments 5-7.

The morroniside and loganin of the present invention all have basic skeleton of iridoid, and can be obtained by extraction from Fructus corni according to known methods, or purchased from market.

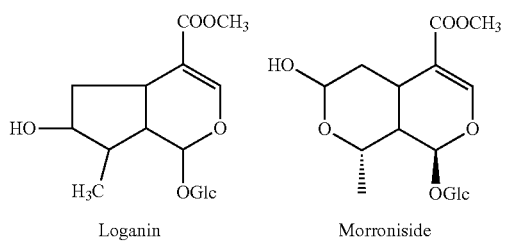

Loganin           Morroniside

For example, the present invention uses a Fructus corni extract obtained by the following extraction method, the analysis shows, relative to the total weight of extract, it comprises 25-50 wt % of morroniside, 25-40 wt % of loganin, and the total content of both is 50-90 wt % of the whole extract.

The method for preparing Fructus corni extract of the present invention comprises the following steps:

(A) water extraction step or water extraction-alcohol precipitation step;
(B) macroporous resin separation step; and
(C) purification step.

The water extraction step preferably comprises decocting Fructus corni crude drug with water for 2-4 times, adding 3-14 times amount of water, performing 1-4 h, combining decoction solutions, filtering and vacuum concentrating.

The water extraction-alcohol precipitation step preferably comprises decocting Fructus corni crude drug with water for 2-4 times, adding 3-14 times amount of water, performing 1-4 h, combining decoction solutions, filtering and vacuum concentrating, adding with ethanol to reach an alcohol concentration of 50-90%, refrigerating for 12-48 h, filtering, recovering ethanol from filtrate under reduced pressure.

The macroporous resin separation step comprises the following steps: providing a concentrated Fructus corni water extraction or water extraction-alcohol precipitation solution, loading on a macroporus resin column, allowing the drug solution to flow through the whole column, performing gradient elution with deionized water, 5-95% ethanol in order, concentrating under reduced pressure to form a fluid extract.

The purification step preferably comprises loading the fluid extract as separated with macroporous resin to $Al_2O_3$ chromatograph column, eluting with ethanol, freeze-drying to obtain a solid product.

Assay method of effective components: performing qualitative analysis of the above extraction product with thin-layer chromatography method; and performing quantitative analysis of the above extract product with high performance liquid chromatography, chromatograph conditions: Lichrospher-C18 column, mobile phase methanol-water (30:70), detection wavelength 240 nm, flow rate 1.0 ml/min. Analysis results: morroniside content is 25-50%, loganin content is 25-40%, the total content of both is 50-90%.

The compounds of the present invention can also be synthesized according to the method known by those skilled in the art.

The present invention further covers, besides the above compounds, the homologs and analogs of these compounds. In this case, the homologs are molecules having a structure substantively similar to that of the above compounds, and the analogs are molecules having substantive biological similarity that is irrelevant to structural similarity.

The present invention further relates to a pharmaceutical composition, and the composition comprises a pharmaceutically acceptable salt formed with an iridoid compound and an organic or inorganic acid.

The compounds of the present invention and their derivatives (derived by oxidation and/or decarboxylation, ring cleavage and/or oxidation ring closure), analogs, homologs, pharmaceutically acceptable salts or hydrates together with a pharmaceutically acceptable carrier or excipient to form a pharmaceutical composition suitable for oral administration. This pharmaceutical composition usually comprises a therapeutically effective amount of any of the above compounds and a pharmaceutically acceptable carrier. Preferably, the effective amount is an amount that can effectively promote proliferation and/or differentiation of nerve cells and is less than the amount causing poisoning in patients.

The preparations of the present invention can comprise any inert excipient commonly used as carrier or diluent, for example, gum, starch, sugar, cellulosic materials, acrylates or mixture thereof. The preferred diluent is microcrystalline cellulose. The composition can further comprise a disintegrating agent (such as cross-linked sodium carboxymethylcellulose) and a lubricant (such as magnesium stearate), and one or more additives, selected from binding agent, buffering agent, protease inhibitor, surfactant, solubilizing agent, plasticizer, emulsifying agent, stabilizing agent, viscosity increment, sweetener, film forming agent, or any combination thereof. In addition, the composition of the present invention can also be in form of controlled release preparation or immediate release preparation.

In one embodiment, the pharmaceutical composition is for oral administration, and thus is formulated in form suitable for oral administration, that is solid or liquid preparation. Suitable solid oral preparations include tablets, capsules, pills, granules, pellets, etc. Suitable liquid oral preparations include solutions, suspensions, dispersions, emulsions, oils, etc.

The term "pharmaceutically acceptable carrier" used in the text refers to any and all solvents, dispersing media, coatings, isotonic agents and absorption delaying agents, and they are compatible to pharmaceutical administration, such as aseptic and pyrogen-free water.

Solid carriers/diluents include but are not limited to gums, starches (e.g., corn starch, pregelatinized starch), sugars (e.g., lactose, mannitol, sucrose, glucose), cellulosic materials (e.g., microcrystalline cellulose), acrylates (e.g., polymethylmethacrylate), calcium carbonate, magnesium oxide, talc, or mixtures thereof.

As for liquid preparations, the pharmaceutically acceptable carrier can be aqueous or nonaqueous solutions, suspensions, emulsions or oils. The examples of nonaqueous solvents include propylene glycol, polyethylene glycol and injectable organic esters, such as ethyl oleate. Aqueous carriers include water, alcohol/water solutions, emulsions or suspensions, including saline and buffered media. Examples of oils include petroleum, oils from animals, plants or synthetic sources, such as peanut oil, soybean oil, mineral oil, olive oil, sunflower oil and fish liver oil. The solutions or suspensions may further comprise the following components: aseptic diluents, such as injectable water, saline solutions, fixed oils, polyethylene glycol, glycerol, propylene glycol, or other synthetic solvents; antibacterial agents such as benzyl alcohol, or methyl p-hydroxybenzoates; antioxidants, such as ascorbic acid or sodium hydrogen sulfite; chelating agents, such as ethylene diamine tetraacetic acid (EDTA); buffering agents, such as acetates, citrates, or phosphates; and tonicity regulating agent, such as hydrochloric acid or sodium hydroxide.

In addition, the composition further comprises a binding agent (e.g., Arabic gum, corn starch, gelatin, Carbomer, ethylcellulose, guar gum, hydroxyl propyl cellulose, hydroxyl propyl methyl cellulose, povidone), disintegrating agents (such as corn starch, potato starch, alginic acid, silica, crosslinked sodium carboxylmethyl cellulose, crosslinked povidone, guar gum, sodium starch hydroxyacetate, Primogel), different buffering agents with pH and ion strength (such as Tris-HCl, acetates, phosphates), additives for preventing surface absorption (e.g., albumin or gelatin), detergent (e.g., Tween-20, Tween-80, Pluronic F68, bile salts), protease inhibitors, surfactants (e.g., sodium lauryl sulfate), osmosis enhancers, solubilizing agents (such as glycerol, polyethylene glycol), glidants (e.g., colloid silica), antioxidants (e.g., ascorbic acid, sodium hydrogensulfite, butylated hydroxyanisol), stabilizing agent (e.g., hydroxypropylcellulose, hydroxypropylmethylcellulose), tackifiers (such as Carbomer, colloid silica, ethylcellulose, guar gum), sweetening agents (e.g., sucrose, aspartame, citric acid), corrigents (e.g., mint, methyl salicylate, orange taste flavoring agent), preservatives (e.g., mercurothiolates, benzyl alcohol, p-hydroxybenzates), lubricants (e.g., stearic acid, magnesium stearate, polyethylene glycol, sodium lauryl sulfate), flow promoting agents (e.g., colloid silica), plasticizers (e.g., diethyl phthalate, triethyl citrate), emulsifying agents (e.g., Carbomer, hydroxypropylcellulose, sodium lauryl sulfate), polymer coatings (e.g., poloxamer or poloxamine), coating and film forming agents (e.g., ethylcellulose, acrylates, polymethacrylates) and/or aids.

The compounds or compositions of the present invention can be consecutively and repeatedly administered for several days to several years. The oral therapy can be sustained for one week to patient's life. Preferably, when the administration is sustained for consecutive five days, the patient may be evaluated to determine whether further administration is necessary. The administration can be in consecutive or intermittent manner, that is, consecutive days of therapy followed by rest period.

The method for preparation of pharmaceutical composition comprising active components is known in the art, for example, mixing, granulating or tableting process. Usually, active components are mixed with excipients that are pharmaceutically acceptable and compatible to the active components. As for oral administration, active reagents are mixed with additives commonly used for this purpose, such as carriers, stabilizers, or inert diluents, then converted by conventional methods into dosage forms suitable for administration, such as tablets, coating tablets, hard or soft capsules, water, alcohol or oil solutions, as above mentioned.

One embodiment is a pharmaceutical composition for oral administration, which comprises an iridoid compound or pharmaceutically acceptable salt or hydrate thereof, microcrystalline cellulose, crosslinked sodium carboxymethylcellulose and magnesium stearate. Another embodiment comprises 50-70 wt % of iridoid compound or pharmaceutically acceptable salt or hydrate thereof, 20-40 wt % of microcrystalline cellulose, 5-15% of crosslinked sodium carboxymethylcellulose and 0.1-5 wt % of magnesium stearate. The composition of another embodiment comprises about 50-200 mg of iridoid compound.

In the preferred embodiment of the present invention, the pharmaceutically composition comprises a common iridoid glycoside; microcrystalline cellulose as carrier or diluent; crosslinked sodium carboxymethylcellulose as disintegrating agent; and magnesium stearate as lubricant. In a particularly preferred embodiment, the iridoid compound is morroniside and/or loganin.

The composition of the present invention can be processed according to a pharmaceutical method to form several clinic pharmaceutical dosage forms, including oral preparations or parenteral preparations. The oral preparation is any one selected from tablets, capsules, pills, granules, suspensions, drop pills, oral liquid preparations; the parenteral preparation is any one selected from injections, aerosols, suppositories or subcutaneous dosage forms.

The aids refer to pharmaceutically acceptable excipients, such as solvents, disintegrating agents, corrigents, preservatives, coloring agent, binding agents.

The iridoid compounds of the present invention such as morroniside and/or loganin can be used for alleviating pathological changes of myelinoclasis of nervous system and inflammatory cell infiltration, promoting formation and plerosis of myelin sheath, reducing inflammatory cytokine content, alleviating nervous function injury; especially for treatment of demyelinating diseases of central and peripheral nervous systems caused by various reasons, including but not being limited to multiple sclerosis, optical neuromyelitis, acute disseminated encephalomyelitis, diffuse sclerosis, concentric circle sclerosis, leukodystrophy, central pontine myelinolysis, acute inflammatory demyelinating polyneuropathy, chronic inflammatory demyelinating polyneuropathy, leukoencephalopathy caused by ischemia-anoxia disease, subacute combined degeneration caused by nutrition deficiency disease, subacute sclerosing panencephalitis or progressive multifocal leukoencephalopathy caused by viral infection, diabetic neuropathy, systemic lupus erythematosus. The present invention can also be used for prophylaxis of the above diseases.

The following examples and experiments further illustrate the present invention, but are not intend to limit the protection scope of the present invention.

EXAMPLE 1

Preparation of Fructus corni Extract

Fructus corni crude drug was decocted with water for 3 times, added with 6 times amount of water, for 2 h. The decoction solutions of the 3 times decoctions were combined, filtered then concentrated under reduced pressure, filtered then refrigerated for use; the concentrated Fructus corni water extract was loaded on HP20 macroporous resin column, and flowed through the whole column, gradient elution was performed with deionized water, 30% ethanol, 50% ethanol, in order, the eluent of 50% ethanol was collected, concentrated under reduced pressure to form an extract; the extract obtained by separation of macroporous resin was extracted with ethanol, subjected to removal of organic solvent, concentration, drying to obtain a solid product. Yield 2.5%.

EXAMPLE 2

Preparation of Fructus corni Extract

Fructus corni crude drug was decocted with water for 3 times, added with 6 times amount of water, for 2 h. The decoction solutions of the 3 times decoctions were combined, filtered then concentrated under reduced pressure, added with ethanol to reach alcohol concentration of 70%, refrigerated for 24 h, filtered, the filtrate was subjected to recovery of ethanol under reduced pressure, refrigerated for use.

The Fructus corni water extraction-alcohol precipitation extract was loaded on HP20 macroporous resin column, and flowed through the whole column, gradient elution was performed with deionized water, 30% ethanol, 50% ethanol, in order, the eluent of 50% ethanol was collected, concentrated under reduced pressure to form an extract.

The fluid extract obtained by macroporous resin separation was loaded on $Al_2O_3$ chromatograph column, purified by ethanol elution, freeze-dried to obtain a solid product. Yield 2.3%.

The analysis by high performance liquid chromatography showed that in the product, the morroniside content was 25-50%, loganin content was 25-40%, and the total content of both was 50-90%.

EXAMPLE 3

Capsules 300 g of Fructus corni extract of the present invention, 1000 g of pharmaceutically acceptable starch, were mixed homogenously, filled in 1# capsules, 0.35 g per capsule, 1-2 capsules for each oral administration, twice per day.

EXAMPLE 4

Tablets 300 g of Fructus corni extract of the present invention, 40 g of carboxymethylcellulose, 50 g of lactose, 4 g of magnesium stearate, were provided. The above components were comminuted, mixed and tableted to from tablets, 0.4 g per tablet, 3 tablets for each administration, 3 times per day.

EXAMPLE 5

Capsules 140 g of morroniside, 120 g of loganin, 1000 g of pharmaceutically acceptable starch, were mixed homogeneously, filled in 1# capsules, 0.35 g per capsule, 1-2 capsules for each oral administration, twice per day.

EXAMPLE 6

Tablets 140 g of morroniside, 120 g of loganin, 40 g of carboxymethylcellulose, 50 g of microcrystalline cellulose, 4 g of magnesium stearate were provided. The above components were communicated, blended, tableted to form tablets, 0.4 g per tablet, 3 tablets per time, 3 times per day.

EXAMPLE 7

Capsules 300 g of morroniside, 200 g of loganin, 800 g of pharmaceutically acceptable starch were filled in 1# capsules, 0.20 g per capsule, 1-2 capsules for each oral administration, twice per day.

EXAMPLE 8

Capsules 400 g of morroniside, 200 g of loganin, 800 g of pharmaceutically acceptable starch mixed homogeneously filled in 1# capsules.

EXAMPLE 9

Capsules 300 g of morroniside, 500 g of loganin, 800 g of pharmaceutically acceptable starch, were mixed homogeneously, filled in 1# capsules.

The tablet composition of Example 6 was used in the following experiments.

Experiment 1: Effects of composition of morroniside and loganin on nervous function score in experimental autoimmune encephalomyelitis (EAE) mice model Preparation of mice model and administration: experimental autoimmune encephalomyelitis (EAE) mice model is an important tool for studying various human nervous system demyelinating diseases. In the present experiment, the preparation of EAE mice model was performed by immunizing female C57BL/6J mice with myelin sheath oligodendroglial cell surface glycoprotein $MOG_{35-55}$. That is, the mice were subcutaneously injected at dorsal part of spinal column with 0.2 mL of $MOG_{35-55}$ antigen elixir, and 0.2 ml of *bordetella pertussis* solution was intraperitoneally injected at the time of immunization injection and 48 h thereafter, respectively. The composition of morroniside and loganin was intragastrically administered after the last injection of *bordetella pertussis* solution, for consecutive 3 weeks.

Nervous function test method: the ethological changes of mice were observed by two experimenters every day using blind method. Scoring standard: 0 score, absence of symptom; 1 score, decrease of tail tension, evident slight gait awkward; 2 score, disappearance of tail tension, moderate gait abnormal, deficient in maintaining gesture; 3 score, limb strength weak; 4 score, limb paralysis; 5 score, near death or died.

Experimental results: after 8 days from immunization, the EAE model mice started to show motor dysfunction, which reached peak on about the $15^{th}$ day. The composition of morroniside and loganin had significant effects on reducing nervous function damage score in model animals (Table 1), which showed that iridoids could facilitate the improvement of clinical symptoms, such as limb numbness, disequilibrium and paralysis, caused by diseases.

TABLE 1

Effects of composition of morroniside and loganin on nervous function damage in EAE mice model at peak of attack

| Group | Animal number | Nervous function damage score |
| --- | --- | --- |
| Normal control | 10 | 0.00 ± 0.00 |
| EAE model | 9 | 2.51 ± 0.32## |
| EAE + prednisone acetate (positive control drug) | 8 | 1.36 ± 0.62** |
| EAE + composition of morroniside and loganin 10 mg/kg | 8 | 2.17 ± 0.87 |
| EAE + composition of morroniside and loganin 30 mg/kg | 8 | 1.75 ± 0.40* |
| EAE + composition of morroniside and loganin 90 mg/kg | 8 | 1.55 ± 0.43** |

Mean ± SD;
$P < 0.01$, comparing model group to normal control group;
*$P < 0.05$,
**$P < 0.01$, comparing drug group with model group.

Experiment 2: Effects of composition of morroniside and loganin on body weight drop in EAE mice model Experimental purpose: body weight drop reflects the break of body immunologic balance. This experiment studies the effects of iridoids on body weight drop in EAE mice model.

Experimental method: the methods for modeling and administration were the same of Experiment 1. The body weight changes of mice were recorded every day. Experimental results: EAE model mice showed body weight drop on about the $10^{th}$ day after immunization, which reached peak on about the $15^{th}$ day. The composition of morroniside and loganin had function of combating body weight drop in model animals (Table 2), which indicated that iridoids could regulate body immune state and combat the body weight drop caused by immune reaction.

TABLE 4

Effects of composition of morroniside and loganin on body weight drop in EAE mice model at peak of attack

| Group | Animal number | Body weight(g) |
| --- | --- | --- |
| Normal control | 10 | 20.32 ± 0.42 |
| EAE model | 9 | 18.78 ± 0.93## |
| EAE + prednisone acetate (positive control drug) | 8 | 20.52 ± 1.19** |
| EAE + composition of morroniside and loganin 10 mg/kg | 8 | 19.48 ± 1.36 |
| EAE + composition of morroniside and loganin 30 mg/kg | 8 | 20.00 ± 0.70* |
| EAE + composition of morroniside and loganin 90 mg/kg | 8 | 20.33 ± 2.48** |

Mean ± SD;
$P < 0.01$, comparing model group to normal control group;
*$P < 0.05$,
**$P < 0.01$, comparing drug group with model group.

Experiment 3: Effects of composition of morroniside and loganin on myelinoclasis of nervous system in EAE mice model Experimental purpose: in this experiment, the pathological changes of myelin sheath of spinal cord in EAE model mice were observed by Luxol Fast Blue (LFB) staining, and the intervention effects of iridoids on these pathological changes were studied.

Experimental method: the mice were anesthetized with 10% chloral hydrate on the $29^{th}$ day of experiment, fixed by perfusion of 4% paraformaldehyde, myeloid tissues were taken for making paraffin sections, section thickness 5 μm. Stained with LFB, observed under microscope, and scored according to the following standard: 0 score, absence of myelinoclasis; 1 score, one small range of myelinoclasis; 2 score, 2 or 3 small ranges of myelinoclasis; 3 score, 1 to 2 large ranges of myelinoclasis; 4 score, large ranges of myelinoclasis accumulatively existing in 20% or more of white matter regions.

Experimental results: EAE model mice had obvious myelinoclasis of spinal cord, while the composition of morroniside and loganin groups had significantly alleviated myelinoclasis (Table 3), which indicated that iridoids could significantly alleviate myelin sheath lesion, and facilitate the prevention of demyelinating diseases of nervous system caused by various reasons.

TABLE 3

Effects of composition of morroniside and loganin on myelinoclasis of spinal cord in EAE mice model

| Group | Animal number | Myelinoclasis (LFB staining score) |
| --- | --- | --- |
| normal control | 3 | 0.00 ± 0.00 |
| EAE model | 3 | 1.78 ± 0.29# |

TABLE 3-continued

Effects of composition of morroniside and loganin on myelinoclasis of spinal cord in EAE mice model

| Group | Animal number | Myelinoclasis (LFB staining score) |
|---|---|---|
| EAE + prednisone acetate (positive control drug) | 3 | 0.81 ± 0.21 |
| EAE + composition of morroniside and loganin 10 mg/kg | 3 | 0.89 ± 0.20** |
| EAE + composition of morroniside and loganin 30 mg/kg | 3 | 0.76 ± 0.17** |
| EAE + composition of morroniside and loganin 90 mg/kg | 3 | 0.68 ± 0.23** |

Mean ± SD;
$p < 0.01$, comparing model group to normal control group;
**$p < 0.01$, comparing drug group with model group.

Experiment 4: Effects of composition of morroniside and loganin on inflammatory cell infiltration of nervous system in EAE mice model Experimental purpose: this experiment was to observe pathological changes of spinal cord tissues in EAE model by hematoxylin-eosin (HE) staining, especially inflammatory cell infiltration situations, and to study the intervention effects of iridoids on these pathological changes.

Experimental method: the mice were anesthetized with 10% chloral hydrate on the $29^{th}$ day of experiment, fixed by perfusion of 4% paraformaldehyde, spinal cord tissues were taken for making paraffin sections, section thickness 5 μm. Stained with HE, observed under microscope, and scored according to the following standard: 0 score, absence of cell infiltration; 1 score, spinal meninge cell infiltration; 2 score, 1 to 4 small ranges of cell infiltration around vessels; 3 score, 5 or more small ranges of cell infiltration around vessels, or one or more accumulatively substantial large range of cell infiltration; 4 score, a large number of cell infiltration ranges accumulatively existing in 20% or more of white matter regions.

Experimental results: EAE model mice had obvious inflammatory cell infiltration in spinal cord tissues, while the model mice administered with the composition of morroniside and loganin had significantly reduced inflammatory cell infiltration (Table 4), which indicated that iridoids could be used for prevention of nervous system demyelinating diseases.

TABLE 4

Effects of composition of morroniside and loganin on inflammatory cell infiltration in spinal cord tissues of EAE mice model

| Group | Animal number | Inflammatory cell infiltration (HE staining score) |
|---|---|---|
| normal control | 3 | 0.00 ± 0.00 |
| EAE model | 3 | 2.08 ± 0.08## |
| EAE + prednisone acetate (positive control drug) | 3 | 1.16 ± 0.12** |
| EAE + composition of morroniside and loganin 10 mg/kg | 3 | 2.11 ± 0.11 |
| EAE + composition of morroniside and loganin 30 mg/kg | 3 | 1.44 ± 0.17** |
| EAE + composition of morroniside and loganin 90 mg/kg | 3 | 1.15 ± 0.18** |

Mean ± SD;
$p < 0.01$, comparing model group with normal control group;
**$p < 0.01$, comparing drug group with model group.

Experiment 5: Effects of composition of morroniside and loganin on content of inflammatory cytokines in EAE mice model Experimental purpose: interleukin-1 (IL-1) and IL-6 are important inflammatory cytokines, and have promoting effects on inflammatory reactions. This experiment used enzyme linked immunosorbent assay (ELISA) to measure contents of IL-1 and IL-6 in serums of EAE mice model, and the effects of iridoids on these contents were observed.

Experimental method: mice were anesthetized with pentobarbital sodium, blood sample was taken from abdominal aorta, stood at room temperature for 2 h, centrifuged at 3000 rpm for 20 min, and supernatant was taken, stored at −80° C. for use. The operation was performed strictly according to the steps of specification of ELISA kit. Optical density was measured with ELIASA at 450 nm. The corresponding contents of IL-1 and IL-6 were calculated with the measured OD values on standard curve.

Experimental results: the mice of EAE model group had serum IL-1 and IL-6 contents significantly higher than those of normal control group; while the composition of morroniside and loganin could reduce the contents of IL-1 and IL-6 in serum of the model mice (Table 5), which indicated that iridoid glycosides could inhibit inflammatory reactions.

TABLE 5

Effects of composition of morroniside and loganin on contents of IL-1 and IL-6 in serum of EAE mice model

| Group | Animal number | 1L-1 content (pg/ml) | IL-6 content (pg/ml) |
|---|---|---|---|
| normal control | 3 | 0.113 ± 0.003 | 0.127 ± 0.002 |
| EAE model | 3 | 0.128 ± 0.005# | 0.142 ± 0.001## |
| EAE + prednisone acetate (positive control drug) | 3 | 0.114 ± 0.001* | 0.124 ± 0.002** |
| EAE + morroniside and loganin 10 mg/kg | 3 | 0.128 ± 0.009 | 0.140 ± 0.001 |
| EAE + morroniside and loganin 30 mg/kg | 3 | 0.113 ± 0.003* | 0.131 ± 0.003** |
| EAE + morroniside and loganin 90 mg/kg | 3 | 0.109 ± 0.003** | 0.123 ± 0.002** |

Mean ± SD;
$p < 0.05$,
$p < 0.01$, comparing model group with normal control group;
*$p < 0.05$,
**$p < 0.01$, comparing drug group with model group.

Experiment 6: Effects of composition of morroniside and loganin on content of oligodendroglial cells of nervous system in EAE mice model Experimental purpose: myelin sheath is formed with prominences of oligodendroglial cells. CNPase (cyclic nucleotide-3'phosphohydrolase) is a marker protein of mature oligodendroglial cells. The present experiment was to measure CNPase content in spinal cord of EAE model mice by Western blot method, and to study the effects of iridoids on expression thereof.

Experimental method: the mice were anesthetized and sacrificed, fresh spinal cord was taken on ice, total protein was extracted by clearage on ice, to prepare Western blot sample, added with CNPase primary antibody and incubated, added with corresponding secondary antibody, ECL colorated, Kodak film exposed. Pictures were analyzed with Image J software and standardized with actin.

Experimental results: in comparison with normal control group, EAE model mice spinal cord CNPase bands became significantly narrow, integration grey level significantly decreased, which suggested the reduction of number of oligodendroglial cell; while in the mice of composition of morroniside and loganin groups, CNPase bands became wide, and integration grey level increased significantly (Table 6). This indicated that iridoids could significantly increase the number of oligodendroglial cells, facilitate the formation of myelin sheath.

TABLE 6

Effects of composition of morroniside and loganin on oligodendroglial cells of spinal cord in EAE mice model

| Group | Animal number | Oligodendroglial cells (CNPase/actin integration grey level) |
|---|---|---|
| normal control | 3 | 1.20 ± 0.05 |
| EAE model | 3 | 1.00 ± 0.12# |
| EAE + prednisone acetate (positive control drug) | 3 | 1.18 ± 0.02* |
| EAE + composition of morroniside and loganin 10 mg/kg | 3 | 1.05 ± 0.03 |
| EAE + composition of morroniside and loganin 30 mg/kg | 3 | 1.08 ± 0.05 |
| EAE + composition of morroniside and loganin 90 mg/kg | 3 | 1.19 ± 0.03* |

Mean ± SD;
P < 0.05, comparing model group with normal control group;
*P < 0.05, comparing drug group with model group.

Experiment 7: Effects of composition of morroniside and loganin on nervous function damage in experimental autoimmune encephalomyelitis (EAE) rats model Preparation of rat model and administration: in this experiment, the preparation of EAE rat model was performed by multipoint immunizing female Lewis rats subcutaneously at tail root with a homogenate of spinal cord and cerebral gray matter of Guinea pig as well as complete Freund's adjuvant after emulsification. They were intragastrically administered with a composition of morroniside and loganin for 3 weeks.

Nervous function test method: the ethological changes of rats were observed by two experimenters using blind method every day. Scoring standard: 0 score, absence of symptom; 1 score, decrease of tail tension, visible evident slight gait awkward; 2 score, double hind limbs weak, walk difficult; 3 score, double hind limbs paralysis; 4 score, double hind limbs paralysis and fore limbs weak; 5 score, four limbs paralysis; 6 score, near death or died.

Experimental results: after 8 days from immunization, the EAE model rats started to show motor dysfunction, which reached peak on about the 12$^{th}$ day. The composition of morroniside and loganin had significant effects on reducing nervous function damage score in model animals (Table 7), which indicated that iridoids could facilitate the improvement of clinical symptoms, such as limb numbness, disequilibrium and paralysis, caused by diseases.

TABLE 7

Effects of composition of morroniside and loganin on nervous function damage in EAE mice model at peak of attack

| Group | Animal number | Nervous function damage score |
|---|---|---|
| normal control | 7 | 0.00 ± 0.00 |
| EAE model | 8 | 3.38 ± 1.32## |
| EAE + prednisone acetate (positive control drug) | 6 | 1.16 ± 1.21** |
| EAE + composition of morroniside and loganin 20 mg/kg | 6 | 2.17 ± 1.21* |

TABLE 7-continued

Effects of composition of morroniside and loganin on nervous function damage in EAE mice model at peak of attack

| Group | Animal number | Nervous function damage score |
|---|---|---|
| EAE + composition of morroniside and loganin 60 mg/kg | 6 | 2.67 ± 1.25* |

Mean ± SD;
P < 0.01, comparing model group with normal control group;
*P < 0.05,
**P < 0.01, comparing drug group with model group.

Experiment 8: Effects of composition of morroniside and loganin on body weight drop in EAE rat model Experimental purpose: body weight drop reflects the break of body immunologic balance. This experiment studies the effects of iridoids on body weight drop in EAE rat model.

Experimental method: the methods for modeling and administration were the same of Experiment 7. The body weight changes of rats were recorded every day.

Experimental results: EAE model rats showed body weight drop after about one week of immunization, which reached peak on about the 12$^{th}$ day. The composition of morroniside and loganin had function of combating body weight drop in model animals (Table 8), which indicated that iridoids could combat the body weight drop caused by immune reaction.

TABLE 8

Effects of composition of morroniside and loganin on body weight drop in EAE rat model at peak of attack

| Group | Animal number | Bodyweight (g) |
|---|---|---|
| normal control | 7 | 225.1 ± 5.6 |
| EAE model | 8 | 182.4 ± 6.1## |
| EAE + prednisone acetate (positive control drug) | 6 | 198.5 ± 7.1** |
| EAE + composition of morroniside and loganin 20 mg/kg | 6 | 196.8 ± 4.7** |
| EAE + composition of morroniside and loganin 60 mg/kg | 6 | 203.8 ± 2.8** |

Mean ± SD;
P < 0.01, comparing model group with normal control group;
**P < 0.01, comparing drug group with model group.

In sum, in many experimental autoimmune encephalomyelitis (EAE) animal models, iridoid compounds such as morroniside and/or loganin showed significant effects on alleviating pathological changes of myelinoclasis of nervous system and inflammatory cell infiltration, increasing the number of oligodendroglial cell to promote the formation and plerosis of myelin sheath, reducing the contents of inflammatory cytokines, lowering nervous function damage score, inhibiting body weight drop caused by immune reaction, which indicated that iridoid compounds are useful in prophylaxis and treatment of demyelinating diseases caused by various reasons.

What is claimed is:

1. A method of treating a disease associated with nervous system myelin sheath lesion in a human or an animal patient, comprising administering to the patient in need thereof a composition comprising morroniside and loganin in a therapeutically effective amount to treat the disease associated with nervous system myelin sheath lesion; wherein the disease is selected from multiple sclerosis and acute disseminated encephalomyelitis.

2. The method according to claim 1, wherein morroniside is 25-50% w/w of the composition, and loganin is 25-40% w/w of the composition.

3. The method according to claim 1, further comprising wherein the composition is an extract of Fructus corni, wherein morroniside is 25-50wt % relative to the total weight of the extract, and loganin is 25-40wt % relative to the total weight of the extract.

4. . The method according to claim 1, wherein the disease is multiple sclerosis.

5. The method according to claim 1, wherein the composition further comprises a pharmaceutically acceptable carrier.

6. The method according to claim 1, wherein the disease is acute disseminated encephalomyelitis.

7. The method according to claim 1, wherein the administering is by oral administration.

8. The method according to claim 1, wherein the composition is a solid oral composition selected from the group consisting of a tablet, a capsule, a pill, a granule, and a pellet.

9. The method according to claim 1, wherein the composition is a liquid oral composition selected from the group consisting of a solution, a suspension, a dispersion, an emulsion, and an oil.

10. The method according to claim 1, wherein the composition comprises an inert excipient.

11. The method according to claim 10, wherein the inert excipient is selected from the group consisting of gum, starch, sugar, cellulosic materials, acrylates, and mixtures thereof.

12. The method according to claim 1, wherein the composition comprises a disintegrating agent.

13. The method according to claim 1, wherein the composition comprises a lubricant.

14. The method according to claim 1, wherein the composition comprises one or more additives selected from a binding agent, a buffering agent, a protease inhibitor, a surfactant, a solubilizing agent, a plasticizer, an emulsifying agent, a stabilizing agent, a viscosity increment, a sweetener, a film forming agent, and combinations thereof.

15. The method according to claim 1, wherein the composition is a controlled release composition.

16. The method according to claim 1, wherein the composition is an immediate release composition.

17. The method according to claim 1, wherein the composition is administered for several days to several years.

18. The method according to claim 1, wherein the composition is administered for consecutive days.

19. The method according to claim 1, wherein the composition is administered intermittently.

* * * * *